(12) United States Patent
de Vries et al.

(10) Patent No.: US 8,892,609 B1
(45) Date of Patent: *Nov. 18, 2014

(54) METHOD AND SYSTEM FOR GENERATING A UNIFIED DATABASE FROM DATA SETS

(71) Applicant: Medidata Solutions, Inc., New York, NY (US)

(72) Inventors: Glen de Vries, New York, NY (US); Michelle Marlborough, Brooklyn, NY (US)

(73) Assignee: Medidata Solutions, Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/450,197

(22) Filed: Aug. 1, 2014

Related U.S. Application Data (63) Continuation of application No. 13/974,294, filed on Aug. 23, 2013, now Pat. No. 8,799,331.

(51) Int. Cl.
*G06F 17/30* (2006.01)
*G06F 19/00* (2011.01)

(52) U.S. Cl.
CPC .... *G06F 17/30528* (2013.01); *G06F 17/30091* (2013.01); *G06F 19/363* (2013.01)
USPC .......................................................... 707/804

(58) Field of Classification Search
USPC .......................................................... 707/804
See application file for complete search history.

(56) References Cited

U.S. PATENT DOCUMENTS

| | | | |
|---|---|---|---|
| 7,464,087 B2 | 12/2008 | Shlaes et al. | |
| 8,234,294 B2 | 7/2012 | Shlaes et al. | |
| 8,676,731 B1 * | 3/2014 | Sathyanarayana et al. | 706/12 |
| 2003/0108938 A1 | 6/2003 | Pickar et al. | |
| 2013/0346356 A1 * | 12/2013 | Welinder et al. | 706/52 |

* cited by examiner

*Primary Examiner* — Alexey Shmatov
(74) *Attorney, Agent, or Firm* — Steptoe & Johnson LLP; Robert Greenfeld (57) ABSTRACT

A method for generating a unified database includes receiving a structured set of data, where each set is made up of records having fields, aggregating values within a first field of the records, automatically applying a set of rules to the first field values to determine correlations among the first field values, calculating a confidence level regarding a label for the first field, providing the label to the first field, storing the first field values in the first field in the unified database, and receiving more information to increase the confidence level. A system for generating a clinical database and a method for using the database are also described.

19 Claims, 11 Drawing Sheets

| BUN | 15 |
|---|---|
| CO2 | 22 |
| Creatinine | 1.0 |
| Glucose | 105 |
| Cl | 106 |
| K | 4.0 |
| Na | 140 |

FIG. 1A

| Systolic BP | 120 |
|---|---|
| Diastolic BP | 80 |
| Heart Rate | 68 |
| Respiratory Rate | 18 |
| Temperature | 37 |

FIG. 1B

| Medication | Aspirin |
|---|---|
| Adverse_Event | Stomachache |
| Start_Date | 12-Jan-2013 |
| End_Date | 13-Jan-2013 |
| Severity | Mild |

| Record | 1 | 2 | 3 | | 400 |
|---|---|---|---|---|---|
| Field 1 | 15 | 14 | 16 | ... | 8 |
| Field 2 | 22 | 22 | 20 | | 28 |
| Field 3 | 1.0 | 0.8 | 0.9 | ... | 1.1 |
| Field 4 | 105 | 120 | 121 | | 78 |
| Field 5 | 106 | 110 | 106 | | 101 |
| Field 6 | 4.0 | 4.1 | 4.3 | ... | 5.0 |
| Field 7 | 140 | 137 | 141 | | 138 |

| Record | 401 | 402 | 403 | ... | 700 |
|---|---|---|---|---|---|
| Field 1 | 120 | 124 | 140 | | 100 |
| Field 2 | 80 | 65 | 85 | | 70 |
| Field 3 | 68 | 75 | 78 | | 72 |
| Field 4 | 18 | 15 | 12 | | 14 |
| Field 5 | 37 | 36.5 | 37.2 | | 37.3 |

| Record | 701 | 702 | 703 | ... | 1200 |
|---|---|---|---|---|---|
| Field 1 | Difenhydramine | Aspirin | Nytroglicerin | | ASPIRIN |
| Field 2 | Headache | Stomachache | Migrain | | Backach |
| Field 3 | 23-Feb-2013 | 12-Jan-2013 | 03-Feb-2013 | | 03-Jan-2013 |
| Field 4 | 25-Feb-2013 | 13-Jan-2013 | 04-Feb-2013 | | 06-Jan-2013 |
| Field 5 | Moderate | Mild | Severe | | Moderate |

METHOD AND SYSTEM FOR GENERATING A UNIFIED DATABASE FROM DATA SETS

CROSS-REFERENCE TO RELATED APPLICATION

This application is a continuation of and claims priority from U.S. application Ser. No. 13/974,294, filed Aug. 23, 2013, now U.S. Pat. No. 8,799,331, the entirety of which is hereby incorporated by reference.

BACKGROUND

Medical testing and clinical trials generate considerable quantities of data. For a multitude of reasons, there has been little success in establishing a comprehensive database of such data. For example, health care professionals often do not perform medical tests in a structured atmosphere whereby the data from those tests may be recorded in a systematic or meaningful way. Additionally, even when medical tests are performed in a structured atmosphere, such as part of a clinical trial, the clinical trial data may be proprietary to the sponsor of the trial, and not shared with other parties such as sponsors, the regulatory agencies, or the public. Moreover, even if the data were to be shared, the data are typically not collected in the same exact format for each test or each trial, resulting in difficulty categorizing the data in a comprehensible way. Furthermore, attempts at categorizing such data have involved extremely labor-intensive manual mapping of data and classifications.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Embodiments of the present invention may be used with respect to clinical data, but the invention is not limited to such embodiments. Embodiments may be used with any data system involving large amounts of data that may exist in data sets. Clinical data includes metabolic data, which may include blood pressure data, heart rate data, and other metabolism data, as well as operational data, which may include monitoring data, such as protocol adherence, adverse events, auto-query rate, early termination rate, and screen failure rate, metadata associated with the collection of metabolic data, or other data related to the gathering or processing of data in clinical trials, such as demographic, enrollment, recruitment, and payment data.

Figure 1A:
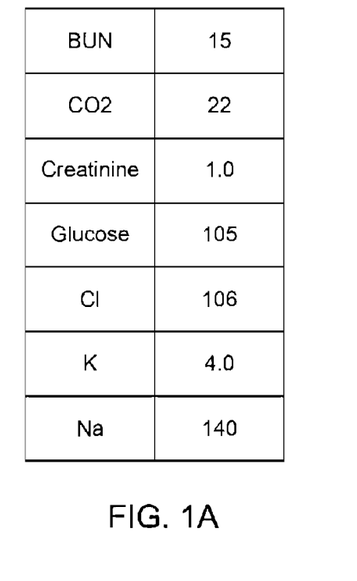
FIGS. 1A-1C are examples of labeled data sets according to embodiments of the present invention.
Figure 1B:
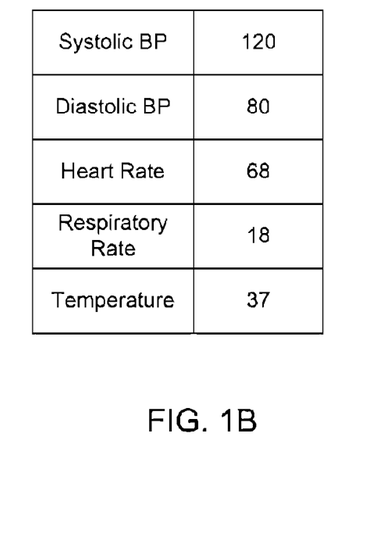
Figure 1C:
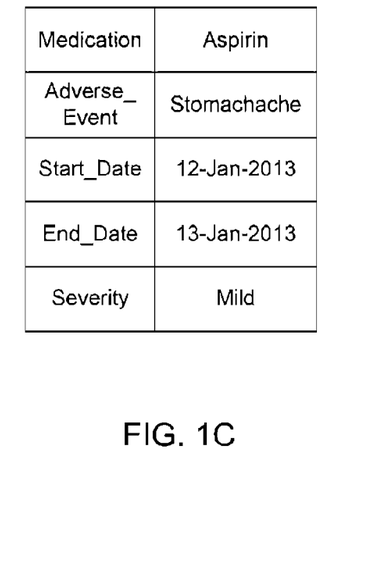

Clinical data are often collected in data sets, and the data may be collected from all types of clinical sources in various clinical settings, including physicals, hospital admissions, medical office visits, clinical trials, off-site or mobile participation in clinical trials, etc. One non-limiting example of such a data set is a "CHEM-7" test or "panel," an illustration of which is shown in FIG. 1A. The "CHEM-7" is a common laboratory test ordered by health care providers and includes a set of seven measurements of chemical constituents of blood, including blood urea nitrogen (BUN), carbon dioxide ($CO_2$) (sometimes called bicarbonate ($HCO_3$)), creatinine, glucose, chloride (Cl), potassium (K), and sodium (Na). This test has a number of names, including SMA-7 (sequential multiple analysis), SMAC-7 (sequential multi-channel analysis with computer), and BMP (basic metabolic panel). Other similar chemical tests are CHEM-8 (which adds Calcium (Ca) to the CHEM-7), CHEM-12, CHEM-20, and a CMP (comprehensive metabolic panel). Other types of diagnostic tests that may be performed in a clinical setting are a CBC (complete blood count), cholesterol tests, blood gas tests, renal tests, urinalysis, CSF (cerebrospinal fluid), and liver and kidney function tests. Often a patient's vital signs or "vitals" are taken, an example of which is shown in FIG. 1B, and these may include systolic and diastolic blood pressure, heart rate or pulse, respiratory rate, and body temperature. Other sets of information that may be recorded in a clinical setting include adverse events or reactions to a medication, an example of which is shown in FIG. 1C, which may include the name of the medication, the adverse event (here, "stomachache"), the start and end dates for the adverse event, and its severity. The description herein is not limited to data from these enumerated tests and panels, and the present invention is applicable to any data collected in a structured data set.

Being able to mine the data may be useful, but because the database labels for these tests (or test types) and their values (field or record names) are not standardized, e.g., some tests may call systolic blood pressure "SYS_BP" and others may call it "SBP," it may not be easy or practical to aggregate the data based on the labels, or to query such data stored in disparate databases. However, there are often typical ranges associated with the values of a test collected within a dataset for a panel, and the tests often appear in a panel in the same location in a data set within a clinical setting.

By using medical and clinical knowledge, understanding the ways that data are collected and organized, knowing statistical distributions of test values, and accessing medical dictionaries and other sources of information, rules may be produced to automatically determine into what category (i.e., what test type) actual data set values should be placed. In other words, even if it is not known a priori that a test value is a systolic blood pressure value, for example, by knowing that the test value is part of a data set that includes five test values, and that the range of all the same test values falls within the range of systolic blood pressure, it may be statistically determined that the test value is a systolic blood pressure value. Each of the test values in the same data set can be analyzed in the same way, and it may be calculated that the other test values comprise diastolic blood pressure, heart rate, respiratory rate, and temperature, which calculation, as described further herein, may provide further confirmation of the identity of the record type (e.g., vitals) and values of the data set as a whole. For example, the fact that there are two data points in each data set with one always greater than the other may help conclude that the two values are systolic and diastolic pressure, rather than, say, height and weight. If the data values are alphabetical, medical and pharmaceutical dictionaries may be used to determine symptoms or medications, and date values may indicate whether the symptoms are adverse reactions to a drug during a clinical trial (an adverse event) or records of events in a patient's medical history.

Once the type of test is known from the test values, the values can then be inserted into a comprehensive database, and uniform labels can be determined for the test type. Labels may be determined in several ways, including that labels may be created based on a pre-determined naming convention, selected from labels which were applied to the known test values, using industry standard labels in SDTM (Study Data Tabulation Model) format, or a combination of these techniques. SDTM is a content standard that describes the core variables and domains to be used as a standardized submission data set format for regulatory authorities such as the U.S. Food and Drug Administration (FDA). Additionally, when data from different clinical sources are analyzed, values from the same test type may be added to the database to generate a more comprehensive database than if the data were taken from just a single source.

Figure 2A:
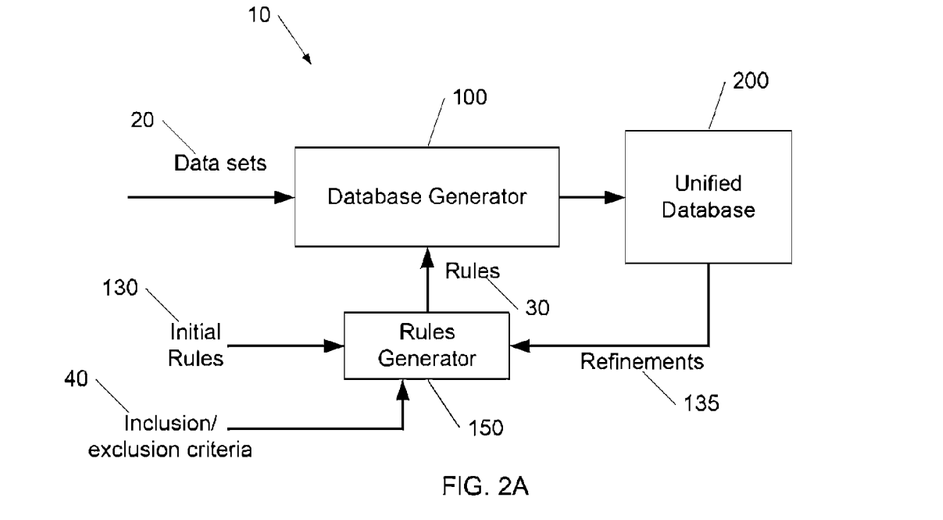
FIG. 2A is a block diagram of a system that includes a database generator, according to an embodiment of the present invention.

Reference is now made to FIG. 2A, which is a block diagram of a system 10 that includes database generator 100 according to an embodiment of the present invention. Data sets 20 may be input to database generator 100 and, based on rules 30, database generator 100 may produce unified database 200.

Rules generator 150 may generate rules 30 for determining how the data in data sets 20 should be analyzed and inserted into the database. It may take as inputs initial rules 130, inclusion/exclusion criteria 40, and refinements 135, which may be generated after database generator 100 reviews one or more data sets.

Data sets 20 may come from one or more sources, including but not limited to EDC (electronic data collection) programs, eCRFs (electronic case report forms) in clinical trials, patient health surveys such as SF-36 forms, patient medical histories, medical databases, and manually-entered data, and may be contained in any of the previous sources in various formats, including record-field-value (R-F-V) format. The data sets may have been recorded in any known format, including ODM (Operational Data Model) format, which is a standard that allows clinical systems to exchange data using XML (Extensible Mark-up Language) and that defines the content and structure of CRFs.

Figure 3A:
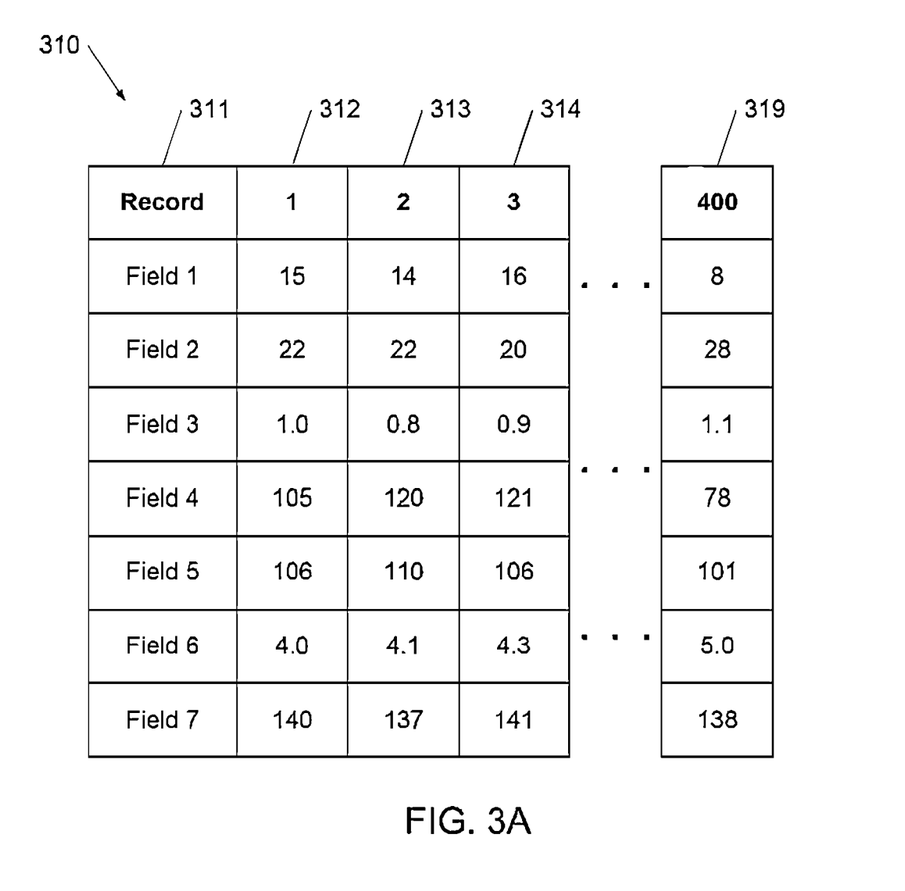
FIGS. 3A-3C are examples of data sets used to generate a unified database, according to embodiments of the present invention.
Figure 3B:
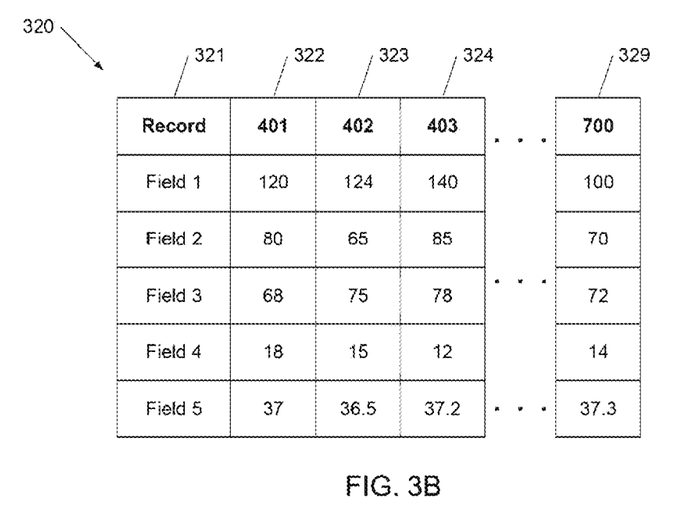
Figure 3C:
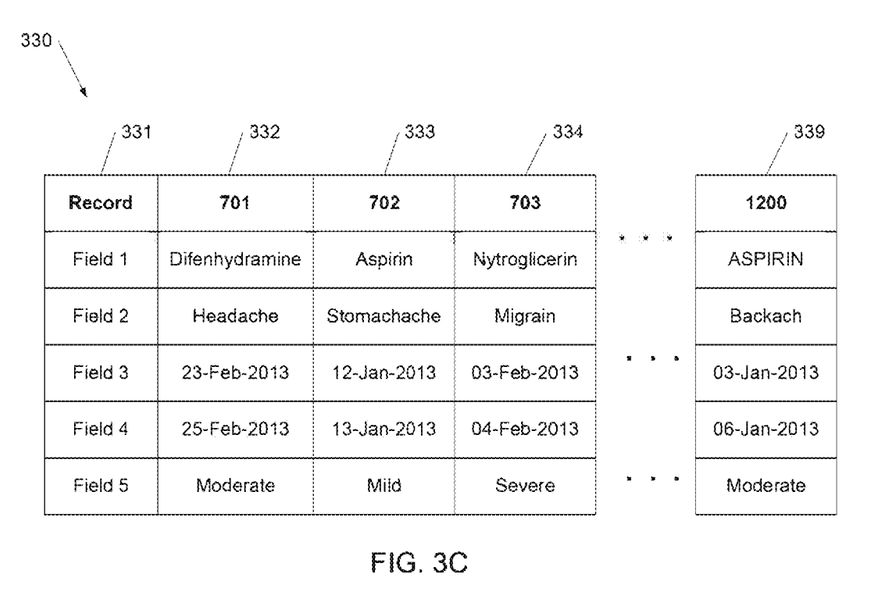

Examples of data sets 20 are shown in FIGS. 3A-3C. These data sets may include any number of records having a number of fields. Example data set 310, illustrated in FIG. 3A, includes 400 records having seven fields, whose values are shown in columns 312-319. The data may come from a single clinical setting, such as a clinical trial, or one or more clinical sources, such as multiple clinical trials or multiple medical histories from hospitals over a period of time. Records from a single source are typically structured in the same way, i.e., the fields are arranged the same in all the records. It is not known a priori what the field labels are in column 311, that is, it is not known what the values in the record are measurements of. Similarly, example data set 320 in FIG. 3B may include 300 records having five fields whose values are shown in columns 322-329, and example data set 330 in FIG. 3C may include 500 records having five fields whose values are shown in columns 332-339.

Figure 2B:
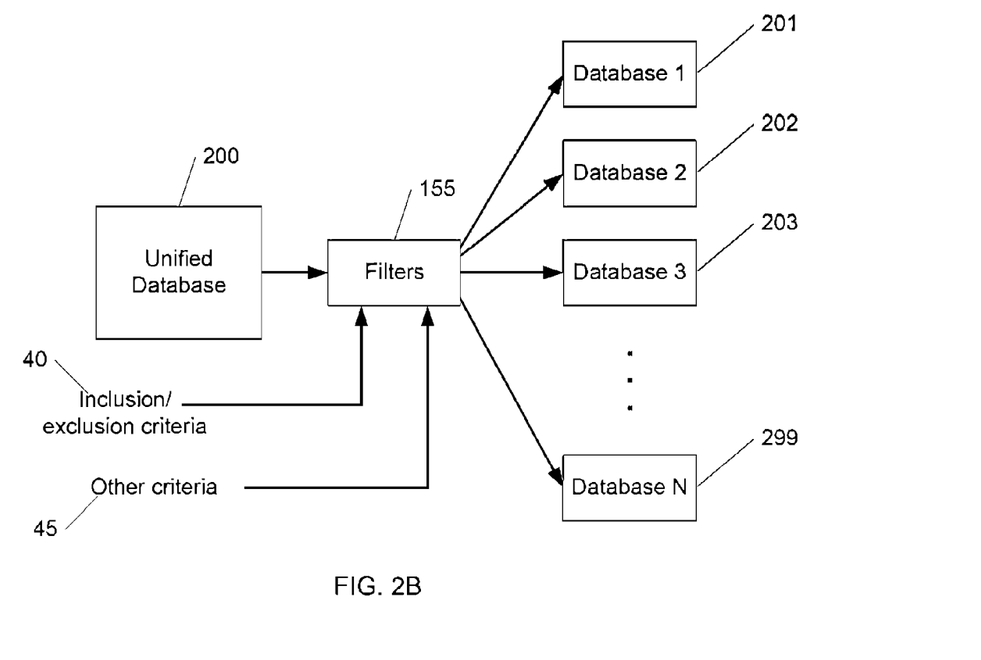
FIG. 2B is a block diagram illustrating a use of a unified database, according to an embodiment of the present invention.

Reference is now made to FIG. 2B, which is a block diagram illustrating a use of unified database 200 according to an embodiment of the present invention. Once unified database 200 has been generated, databases 201, 202, 203, 299 (and others) may be generated using filters 155 and may then contain subsets of unified database 200. The filters may be inclusion/exclusion criteria 40 or other criteria 45, such as chemical tests, vital test values, adverse events, type of study (e.g., hypertension study, pain study, etc.), therapeutic area (e.g., oncology, cardiology, etc.), or one or more rules 30. Then, databases 201, 202, 203, 299 may be generated as one or more chemical lab test databases, a vital signs database, or an adverse events database. Other examples of databases generated may include a demographics database, a concomitant medication database, or a procedure-based database. A concomitant medication is a drug or biological product taken by a subject during a clinical trial, that is different from the drug being studied. A procedure-based database may include a set of data that includes a quantitative analysis measuring some aspect of a condition, for example, analysis of how a tumor looks.

Thus, the data sets input to database generator 100, as well as databases 201, 202, 203, 299 ultimately generated, may include any data, including actual patient or clinical data or data that is computed from actual patient or clinical data. Moreover, databases 201, 202, 203, 299 do not have to be static, but can be generated and regenerated based on the content of unified database 200, which itself may change as more data are added to it. Databases 201, 202, 203, 299 may also be virtualized databases, that is, they may virtually or logically be situated as a database layer above a physical database, such as unified database 200.

Figure 4A:
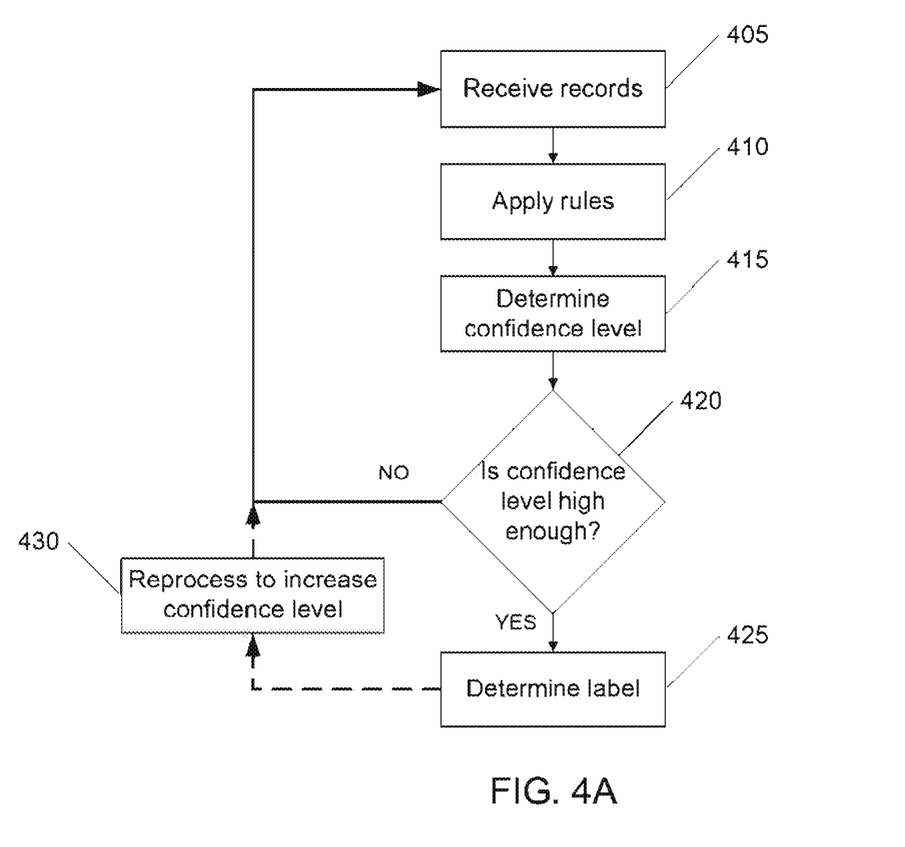
FIG. 4A is a flowchart illustrating how a unified database may be generated, according to an embodiment of the present invention.

FIG. 4A is a flowchart illustrating how unified database 200 may be generated, according to an embodiment of the present invention. In operation 405, records that may include structured data sets 20 are received or collected, for example by database generator 100.

In operation 410, rules may be applied to a record and/or to a field in the record. One rule that may be applied is to determine the type of field, for example, a numeric field, a text or alphabetical field, an alphanumeric field, or a date or chronological field. Another rule that may be applied is to determine the environment in which the data were collected, such as clinical or economic or physical, etc. Another rule that may be applied is to determine the type of record, or perhaps just that the current type of record is the same as the previous record or set of records. Another rule that may be applied in the clinical environment is to determine the patient to whom the record relates, or perhaps just that the current record relates to the same patient as did the previous record or set of records.

Other rules may include determining correlations or statistics among fields within a record, between fields of different records, or between records themselves. These rules may include comparisons between the current fields and/or records and, for example, stored statistics and distributions of known clinical measures or test types for numerical values, dictionary entries for alphabetical and alphanumeric values, and stored calendar information for date values.

In operation 415, a measure of statistical confidence, such as a confidence level or confidence coefficient, of the correlations may be determined. Operation 420 asks if the confidence level is high enough. If not, for example, it does not exceed a predetermined threshold, more information may be needed, possibly from reviewing more records, reviewing other fields within the records, applying more rules, or refining the rules (not all of these options are illustrated in FIG. 4A). If the confidence level is high enough, in operation 425 the field and/or record values may then be classified or labeled and put in unified database 200, possibly along with the confidence level. In operation 430, the fields and/or records may be re-processed after, for example, reviewing more records, reviewing other fields within the records, applying more rules, or refining the rules, in order to increase the confidence level at a later time.

Figure 4B:
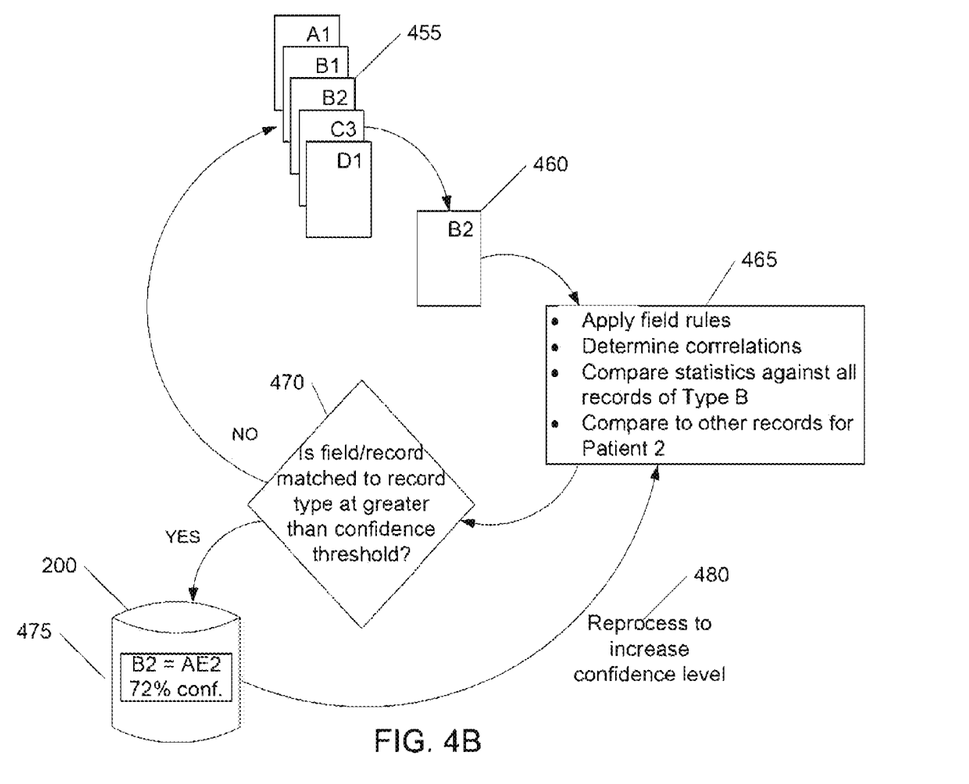
FIG. 4B is a flow diagram illustrating how a unified database may be generated, according to another embodiment of the present invention.

FIG. 4B is a flow diagram illustrating how unified database 200 may be generated, according to another embodiment of the present invention. Records 455, which may include structured data sets 20, may be received or collected, for example by database generator 100. These records may be of types A, B, C, D, etc. for subjects or patients 1, 2, 3, etc. In the clinical data context, types A, B, C, and D may be Chem-7 panels, vitals, adverse events records, etc. Record B2 460, which is a record of type B for subject 2, may be extracted from records 455, and the contents of B2 may be analyzed. In operation 465, such analysis may include applying rules 30 to each field, determining correlations among the fields and/or records, comparing statistics against all records of type B, and comparing the values in record B2 against other records for subject 2. As an example of the latter instance, if a subject is in a clinical trial and the date of the subject's entrance into the clinical trial is known, then information associated with a date after the entrance date may be related to the trial and may be an adverse event due to the drug under test, whereas information associated with a date before the entrance date may be related to the subject's medical history. After comparing the information in operation 465 and applying the rules, operation 470 asks whether the field and/or record can be matched to a record type at greater than a pre-determined confidence threshold. If so, then the field and/or record can be classified, for example, as an "adverse event" record for patient 2 (see label 475 showing "B2=AE2"), with a confidence level of 72%, and placed in unified database 200, which may be a clinical data repository (CDR). Even if the confidence threshold is reached, the flow may proceed via operation 480 to reprocess the field and/or record in operation 465 to try to increase the confidence level, perhaps based on more records, better statistics, better rules, or more information. If the response in operation 470 is that the confidence threshold is not reached, then the flow may return to records 455 to access more information in order to classify the field and/or record.

Figure 5:
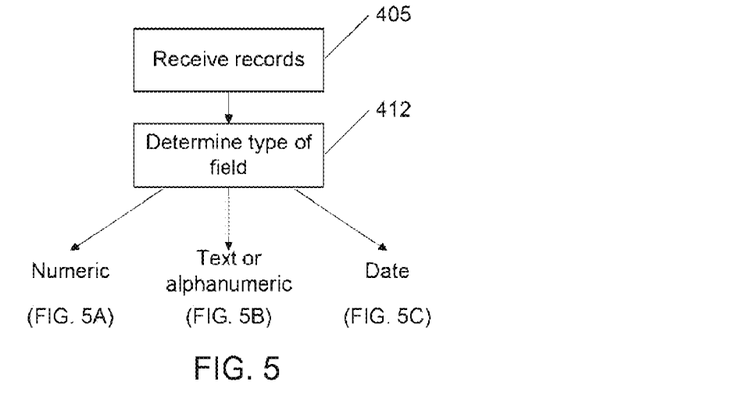
FIGS. 5-5C are flowcharts illustrating how a unified database may be generated using clinical data, according to further embodiments of the present invention.
Figure 5A:
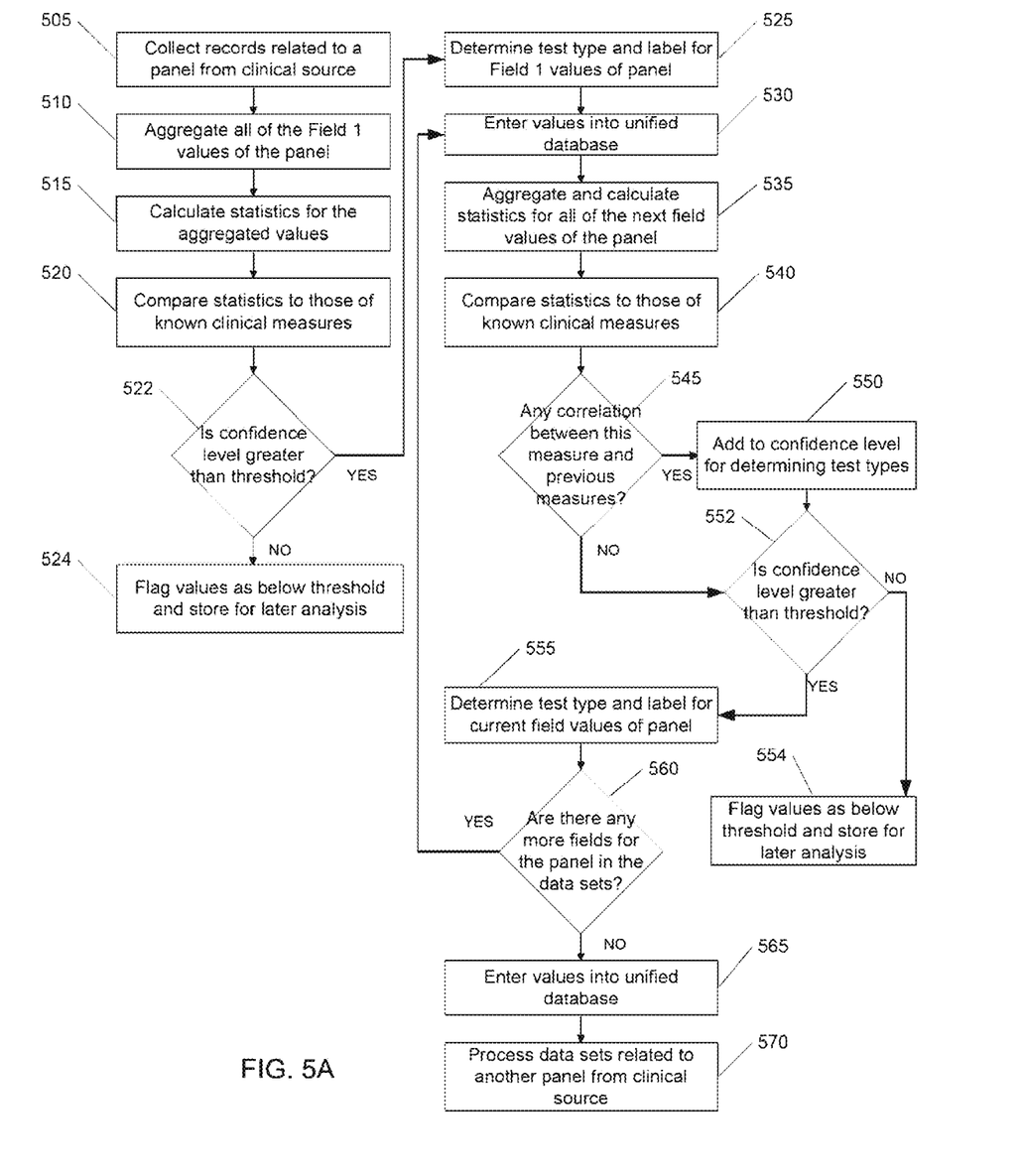
Figure 5B:
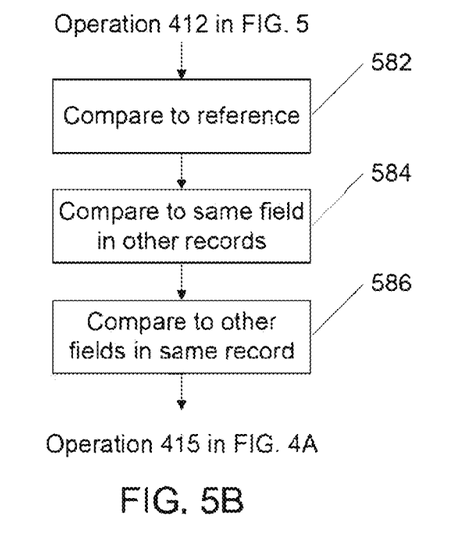
Figure 5C:
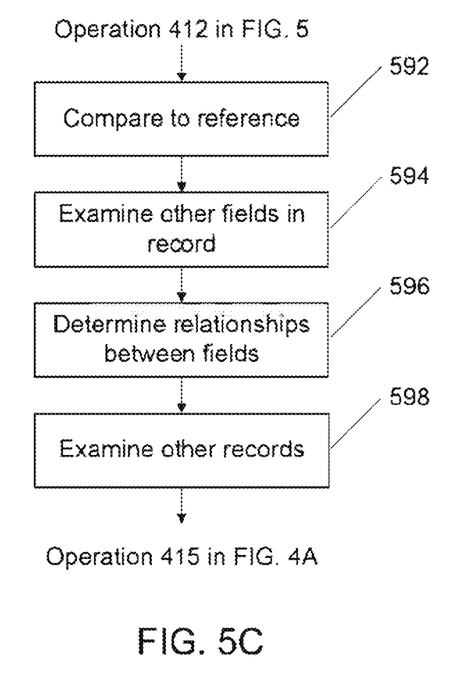

FIGS. 5-5C are flowcharts illustrating how unified database 200 may be generated using clinical data, according to further embodiments of the present invention. In FIG. 5, as in FIG. 4A, in operation 405, records that may include structured data sets 20 are received or collected, for example by database generator 100. In operation 412, a rule that may be applied is to determine the type of field that is being analyzed. This may be, for example, a numeric field, a text or alphabetical field, an alphanumeric field, or a date or chronological field. FIGS. 5A-5C are flowcharts that illustrate these possibilities.

FIG. 5A is a flowchart illustrating how unified database 200 may be generated using numeric clinical data, according to an embodiment of the present invention. In operation 505, records related to a panel from a clinical source (e.g., medical office, hospital visit, clinical trial, etc.) may be collected. A panel may be any group of test measurements that are taken together, e.g., in a data set. In FIGS. 3A-3C, there are a seven-value panel, a five-value panel, and another five-value panel. For illustration purposes, assume there are 300 records related to five-value panel 320. In operation 510, all of the Field 1 values (300 values) of the panel in the records may then be aggregated. Referring to FIG. 3B, this means that the 120, 124, 140, . . . 100 values are aggregated and, in operation 515, all of the aggregated values may be analyzed to calculate statistics for the aggregated values. Statistical calculation may include plotting the values and determining mean, median, mode, range, and standard deviations and variances. In operation 520, the statistics of the fields being analyzed may then be compared to stored statistics and distributions of known clinical measures (or test types). In some cases, such as if only the raw data of known clinical measures are stored rather than their statistics and distributions, the statistics and distributions of the stored data may be calculated as well as the statistics of the current field values.

Figure 6A:
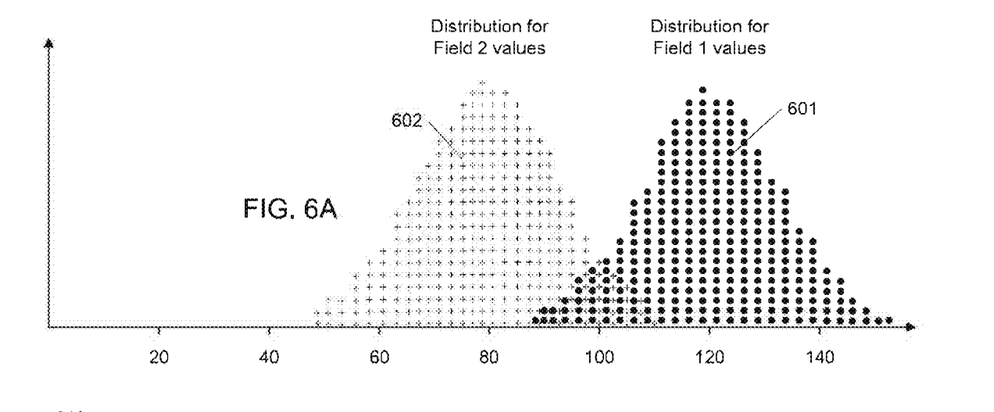
FIGS. 6A-6C are diagrams illustrating how distributions of data may be matched to known clinical value distributions, according to embodiments of the present invention.
Figure 6B:
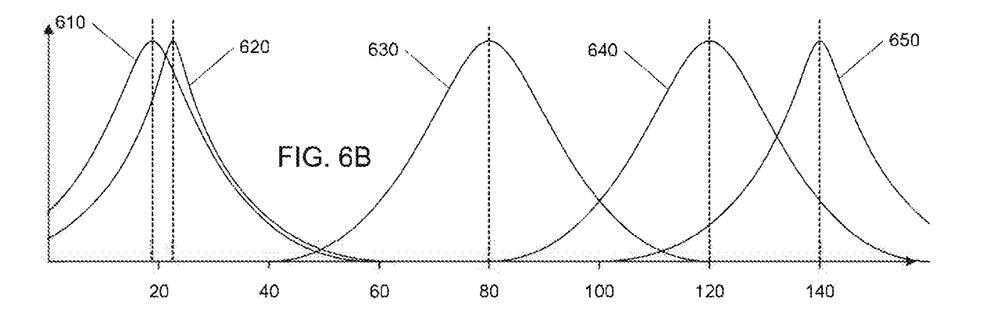
Figure 6C:
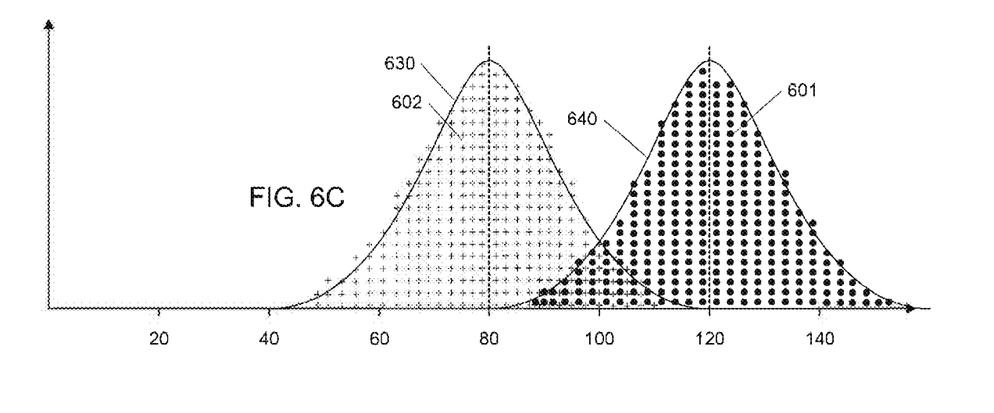

Referring to FIG. 6A, data points 601 (circles) may represent the distribution of all the Field 1 values aggregated from the panel. This distribution may be compared to the distributions of a number of known, stored clinical measures, including but not limited to heart rate, respiratory rate, $CO_2$ (carbon dioxide or bicarbonate), Cl (chloride), Na (sodium), diastolic blood pressure, systolic blood pressure, and the measures shown in FIGS. 1A-11C. FIG. 6B shows statistical distributions and means for five of these clinical data measures—respiratory rate 610, $CO_2$ 620, diastolic blood pressure 630, systolic blood pressure 640, and sodium (Na) 650. The comparison of the calculated statistical distributions of Field 1 values with distributions of known, stored clinical measures may also contribute to determining a confidence level.

In operation 522, the confidence level may be compared to a threshold value, which threshold value may be pre-determined or received from a user of the method and system of the present invention. For the numeric values plotted in FIG. 6A, if the confidence level exceeds the threshold level, it may be determined that the distribution of data points 601 most closely resembles distribution 640, which is the distribution of systolic blood pressure. Because the distributions compare favorably, it may be determined in operation 525 that the aggregated Field 1 values represent the test type systolic blood pressure, and the values may be given the label "SYS_BP" or any other suitable label.

The confidence level may also be stored and be further modified as described below with reference to operations performed on values from subsequent fields and records. For example, if the confidence level does not exceed the threshold level in operation 522, further operations on Field 1 values, including but not limited to determination of a label for Field 1 values in 525, may not be possible. Field 1 values and the results of their calculated statistical distribution may then be flagged in operation 524 as unsuccessfully determined and may be stored for subsequent operations utilizing other successfully determined field values within the same data set.

Figure 7A:
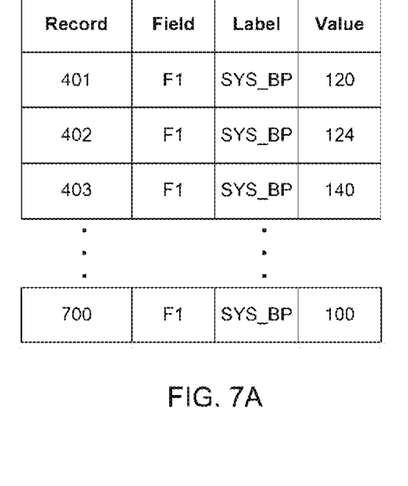
FIGS. 7A-7C are examples of entries in the unified database, according to embodiments of the present invention.

Based on the determination in operation 525, the 300 values from Field 1 of data set 320 may be entered into unified database 200 in operation 530. The result is shown in FIG. 7A, which contains Record Number, Field Number, Label, and Value field or record names.

The Field 2 values of the panel (the 80, 65, 85, . . . 70 values in Field 2 for records 401, 402, 403, 700 in FIG. 3B) may then be aggregated in operation 535 and analyzed to calculate statistics, which is similar to the functions performed in operations 510 and 515, including but not limited to plotting the values and determining mean, median, mode, range, and standard deviations and variances. In operation 540, the statistics may then be compared to stored statistics and distributions of known clinical measures, just as in operation 520. As with operation 520, in some cases, such as if only the raw data of known clinical measures are stored rather than their statistical results and distributions, the statistical results and distributions of the stored data may be calculated as well as the statistical results of the current field values.

Referring to FIG. 6A, data points 602 (plusses) may represent the distribution of all the Field 2 values collected from the panel. This distribution may be compared to the distributions of a number of known, stored clinical measures, including but not limited to heart rate, respiratory rate, $CO_2$ (carbon dioxide or bicarbonate), Cl (chloride), Na (sodium), diastolic blood pressure, systolic blood pressure, and the measures shown in FIGS. 1A-1C. Examining the distributions in FIG. 6B, it may be initially determined that the distribution of data points 602 most closely resembles distribution 630, which is the distribution for diastolic blood pressure.

Since the data for Field 1 have already been analyzed and determined to be systolic blood pressure, operation 545 may ask whether there is any correlation between the Field 2 measure and the Field 1 measure. Because a correlation between systolic and diastolic blood pressure may be known to exist (e.g., as part of rules 30, discussed further below) in the same panel, in operation 550, the confidence level for determining labels may be increased for both the Field 1 and Field 2 values. Even if the Field 2 measures were not correlated with the Field 1 measure (or other previous measures), for example, if the Field 1 values were determined to represent sodium (Na), there may still be sufficiently high statistical confidence that the Field 2 measure still represents diastolic blood pressure based on the statistical analysis and calculation discussed above.

As with the Field 1 values, the comparison of the calculated statistical distributions of Field 2 values with distributions of known, stored clinical measures may also contribute to determining the confidence level, which may be compared to a threshold value. As before, the threshold value may be predetermined or received from a user. If, in operation 552, the confidence level exceeds the threshold level, then, in operation 555, the aggregated Field 2 values may be determined to represent the test type diastolic blood pressure, and the values may be given the label "DIAS_BP" or any other suitable label.

The confidence level may again be stored and be further modified based on operations performed on values from subsequent fields and records. If, in operation 552, the confidence level does not exceed the threshold level, further operations on Field 2 values, including determination of a label for Field 2 values in operation 555, may not be possible. Field 2 values and the results of their calculated statistical distribution may be flagged in operation 554 as unsuccessfully determined and may be stored for subsequent operations utilizing other successfully determined field values within the same data set.

Figure 7B:
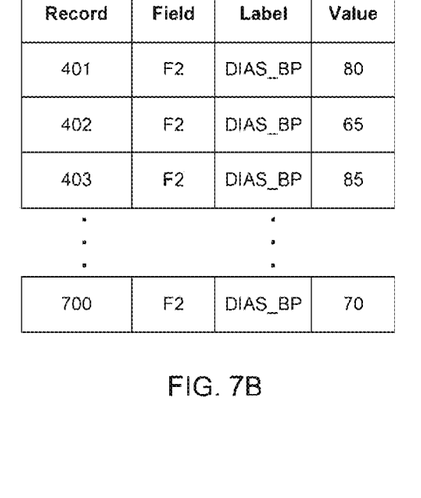

After labeling the current field measure, operation 560 may then ask whether there are any more fields for the panel in the data sets. If so, the process may loop back to operation 530 to enter the field values into unified database 200. The result is shown in FIG. 7B, which contains Record Number, Field Number, Label, and Value field or record names. If there are no more fields for the panel in the data sets, the field values may be entered into unified database 200 in operation 565, and then in operation 570 the process turns to the next group of data sets related to a different panel.

Referring to FIG. 5, if in operation 412 it is determined that the field type is text or alphanumeric, then the flowchart in FIG. 5B may be followed. In operation 582, the field value, e.g., a word or phrase, may be compared to a reference, such as a dictionary. If the data is clinical data, a medical dictionary may be used. Examples of such dictionaries may include MedDRA (Medical Dictionary for Regulatory Activities), which includes information about medical terminology and may be used for coding adverse events, clinical signs and symptoms, procedures, investigations, indications, and medical and social histories; and the WHO (World Health Organization) Drug Dictionary, a dictionary that includes medicinal product information. Thus, the system may look into MedDRA for accepted adverse events or look into WHO Drug for accepted names of medications. For example, Field 1 in record 701 in FIG. 3C includes "Difenhydramine" [sic], but that word does not appear in MedDRA or WHO Drug. A close word in WHO Drug is "Diphenhydramine," which is an antihistamine. In order to determine if this is the correct word, it may be useful to compare the word in Field 1 in record 701 to the words in Field 1 in the other records, as shown in operation 584, which may be considered a type of aggregation. There may be other instances of the word spelled the same, or a close word with a different spelling. In the case of FIG. 3C, other Field 1 values are "Aspirin," "Nytroglicerin" [sic], and "ASPIRIN." While "Aspirin" is spelled correctly, the system may recognize "Nytroglicerin" as "Nitroglycerin" and "ASPIRIN" as "Aspirin." If the system is still not sure what the word is, in operation 586 it may examine other fields in the same record. Once those comparisons are made, the flow returns to operation 415 in FIG. 4A to determine the confidence level and then determine whether the confidence level is high enough. If so, in operation 425, the field is given a label, in this case, possibly "Medication" or "Concomitant Medication."

If the confidence level is not high enough, then more Field 1 values may be examined or aggregated in order to determine the correlations among the values, or the system may process Field 2 values in order to understand more about the record values or record type and possible relationships among the fields. For example, the system may identify the Field 2 values of "Headache," "Stomachache," "Migrain" [sic], and "Backach" [sic]" as "Headache," "Stomach ache," "Migraine," and "Back ache." The system may label this field as "Adverse_Event," and then determine that the Field 1 values are not only medications, but are concomitant medications, and label Field 1 accordingly.

Referring again to FIG. 5, if in operation 412 it is determined that the field type is a date, then the flowchart in FIG. 5C may be followed. In operation 592, the field value may be compared to a reference, such as a stored calendar. Different references may be used depending on the environment in which the data were collected. A stored calendar may include dates derived from other fields or other records and may relate to a particular patient if the data is clinical. In operation 594, the system may examine other fields in the records and, in operation 596, may determine relationships between fields, such as whether two dates are paired with each other, one field's date values are always before or after another field's date values, or whether the dates are before or after certain milestone dates related to a particular patient. If the system is still not sure what the date indicates, in operation 598 it may examine the same fields in other records to determine possible relationships and correlations among the records. Once those comparisons are made, the flow returns to operation 415 in FIG. 4A to determine the confidence level and then determine whether the confidence level is high enough. If so, in operation 425, the field is given a label, in this case, possibly "Start Date" or "End Date" or "Date of Service." If the confidence level is not high enough, then the system may process values from other fields in order to understand more about the record values or record type and possible relationships among the fields. For example, the system may identify the Field 5 values in FIG. 3C of "Moderate," "Mild," and "Severe," and may label this field as "Severity," and then determine that the date field values may indicate adverse event start or end dates and label those fields accordingly.

Figure 7C:
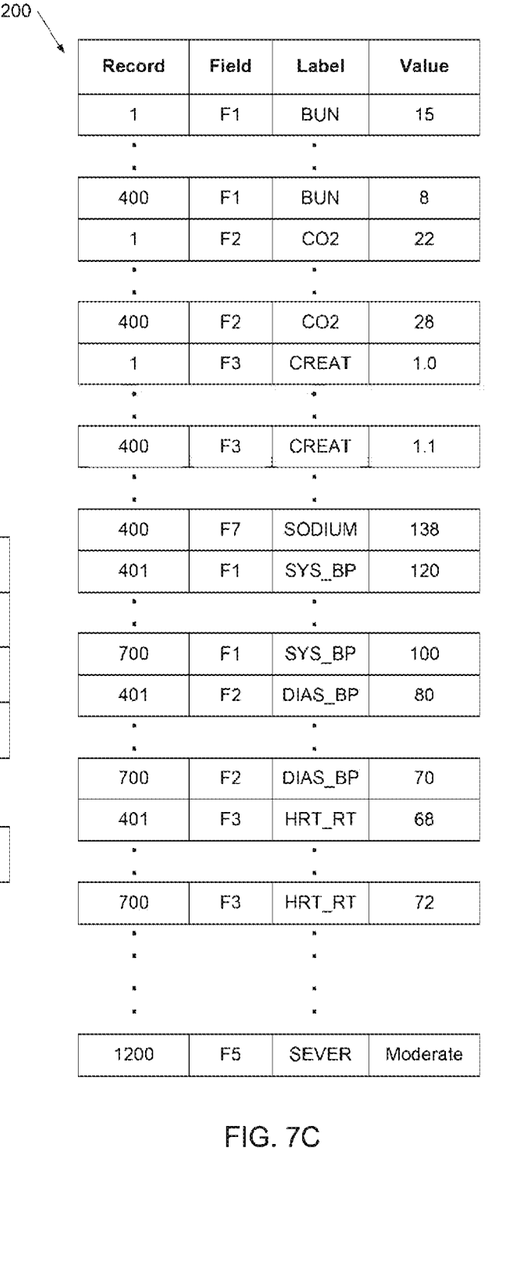

FIG. 7C shows the results after processing the 1200 records in the panels shown in FIGS. 3A-3C and performing the analysis and calculations. Unified database 200 includes 400 records for seven-value panel 310, which is a CHEM-7 panel, 300 records for five-value panel 320, which is a vital signs panel, and 500 records for five-value panel 330, which is an adverse events panel. In all, unified database 200 in this example has 6800 rows (400*7+300*5+500*5) for the three panels. The data may be arranged according to SDTM (Study Data Tabulation Model) format or other standard format. Not shown in FIGS. 7A-7C are other fields that may be retained in unified database 200, such as a patient ID, the clinical setting or clinical trial from which the data originally came, and the drug under study (if a clinical trial), among others.

Besides the operations shown in FIGS. 4A, 4B, and 5-5C, other operations or series of operations may be contemplated to generate a unified database. For example, in FIG. 5A, field values are described as being separately aggregated and then analyzed, but in other embodiments multiple fields could be analyzed together in order to determine the record type. Steps shown in FIGS. 5A, 5B, and 5C may be used in each of the other flowcharts to determine field values, record types, or field labels. In addition, although field types described are numeric, alphabetical, alphanumeric, and date, other types of fields may exist in the data sets and be analyzed and processed by the system.

Moreover, the actual orders of the operations in the flowchart in FIGS. 4A, 4B, and 5-5C are not intended to be limiting, and the operations may be performed in any practical order. For example, although labels are entered into unified database 200 in operations 530 and 565 in FIG. 5A, entries into the database may be made at the end of processing all of the data sets. And fields may be analyzed in conjunction with other fields in the same record or across the same field or other fields in other records. The general object of the operations in FIGS. 4A, 4B, and 5-5C is to generate a unified database by inputting data values from data sets, detect or determine correlations among the data based on rules 30, and determine the labels for the values, fields, and records.

As mentioned above, system 10 may include rules generator 150 that generates rules 30 that are fed into database generator 100. There may be initial rules 130, which may be able to calculate 80-90% of the field values to determine a label for each value. After the system has processed the data, patterns may be revealed that were not known and captured as initial rules. This is where refinements 135 may enter the system and process some or all of the remainder of the field values. If data values still cannot be correlated even after the refinements, they may remain as data sets until more information is received or rules are developed or refined later. Then calculations may be made with these data values using the new rules so that unified database 200 may include these results.

Figure 8:
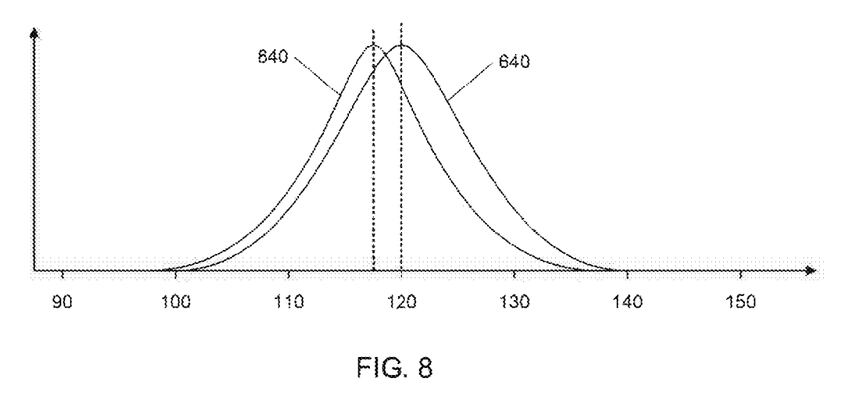
FIG. 8 is a diagram illustrating different distributions of systolic blood pressure, according to an embodiment of the present invention.

Initial rules 130 may include but are not limited to information about adverse events from MedDRA and about drugs from WHO Drug. Initial rules 130 may also include the statistical distributions and mean, median, mode, range, and standard deviations and variances for the various clinical test types that the system may encounter, including the metabolic panels, vital signs, blood gas readings, blood tests, and urinalyses. Initial rules 130 may also include known correlations among the fields and values within a panel, e.g., if systolic blood pressure is labeled, then diastolic blood pressure should also be labeled in the same panel; if a data set has 20 fields, it may well be identified as a CHEM-20 panel; or if there is a "start date" there may be an accompanying "end date." Initial rules 130 may include information about the format of records, e.g., record-field-value format, and the typical order of test types within panels, such as a CHEM-7 panel. Initial rules 130 may also include variations or combinations of statistical information based on age, gender, weight, height, and other demographic information. For example, FIG. 8 illustrates systolic blood pressure distribution 640, which is for the population as a whole, and distribution 840, which may be systolic blood pressure for those without a history of hypertension. This data may be used to identify or modify a field label, possibly in connection with the inclusion/exclusion criteria 40. To do this, inclusion criteria may be parsed to produce a set of logical statements that describe the patient population and allow the system to apply the appropriate clinical distributions. For example, if it is known that some data sets were collected using inclusion/exclusion criteria that separated out those without a history of hypertension, e.g., there may be an inclusion criterion that says, "does not have hypertension," then the data from those sets that correspond to systolic blood pressure may appear in unified database 200 under the label "SYS_BP_NO_HYP," rather than just "SYS_BP."

Once unified database 200 is generated it can be used in a number of ways. As illustrated in FIG. 2B, information can be placed in smaller databases, such as virtualized or physical databases 201, 202, 203, and 299. These databases may be similar to the data sets that were used to generate unified database 200, but they may have more comprehensive data, e.g., not just data from a single clinical trial, and may have uniformly-labeled fields. So, database 201 may be a Chem-7 database, database 202 may be a vitals database, database 203 may be an adverse events database, and database 299 may be a concomitant medication database. These databases can be used by drug sponsors, hospitals, clinics, and information processing systems.

Another way to use unified database 200 is in other, subsequent clinical trials. Often a trial will be designed with a placebo arm in order to measure the effects of the drug under test in a random and blinded fashion. But in many countries, it is not ethical or permissible by regulation to perform placebo tests with patients who are in dire need of the drug under test, because some patients will not actually receive the drug. Using this unified database 200 (or databases 200, 201, 202, 299) in combination with inclusion/exclusion criteria 40 from prior clinical trials, placebo arms can be developed using relevant data from previous clinical trials. Inclusion/exclusion criteria, which may be used as filters, may include minimum age, maximum age, gender, weight, pre-existing medical conditions, and others. So long as the inclusion/exclusion criteria for the previous clinical data match that of the drug under test, the results of the active (drug-taking) arm of a current clinical trial can be compared with the placebo arm of the previous clinical trial.

Such inclusion/exclusion criteria may also come from protocol databases. An example of a protocol is shown below:

|               | Visit 1 | Visit 2 | Visit 3 | Visit 4 | Visit 5 |
|---------------|---------|---------|---------|---------|---------|
| Vitals        | ✓       | ✓       | ✓       | ✓       | ✓       |
| Lab 1         | ✓       |         | ✓       |         | ✓       |
| Lab 2         | ✓       |         |         | ✓       |         |
| Tumor volume  | ✓       | ✓       | ✓       | ✓       | ✓       |
| Medical History | ✓     |         |         |         |         |

The table shows the protocol followed at each visit, as follows: Vital signs are recorded and tumor volume is measured at every visit, medical history is taken at the first visit only, and Lab 1 and Lab 2 are taken at the first visit and then selected visits afterward. Knowing the protocol used to develop the data sets also helps determine the labels for the different test types in the data sets.

The data in unified database 200 can also be used in predictive ways. For example, the data can be used to forecast how a clinical trial (or part of a clinical trial) may run its course. Using operational (e.g., trial enrollment, recruitment, payment, etc.) data, one may examine how long it took study sites to recruit their cohorts of subjects using the inclusion/exclusion criteria for their studies. Collecting this type of data in the database may allow a sponsor to see what the effects of using different inclusion/exclusion criteria would be on how long it takes a study site to recruit its cohort, and the sponsor can therefore select its criteria based on desired, predicted recruitment time or at least have a better idea of how long the recruitment phase for a study may take (and cost), so that it can better prepare its study budget.

As another example, if data in unified database 200 shows a correlation between elevated levels of a certain metabolite and an increased risk of heart attack, then that information can be used to look for patients with elevated levels of that metabolite in order to intervene before the predicted heart attack occurs, or to investigate why some patients did not suffer a heart attack.

Moreover, data that are categorized and placed in unified database 200 may be useful to automate processes that are now performed manually. For example, as mentioned above, the data may be arranged in SDTM format, which can be used to submit data in an automated manner to a regulatory agency, such as the FDA, rather than submitting the data in a text-based format. Currently, the FDA requires data to be submitted in SDTM format, so sponsors and their agents often expend much effort transforming clinical trial data into SDTM format. The present invention thus may save a clinical trial sponsor time and money in preparing its regulatory documentation. In addition, unifying the data in a standardized format (e.g., SDTM and/or ODM) may allow it to be used in many companies' database systems in the event that they want to analyze the data in the context of their own projects.

Prior approaches to developing clinical data databases have been to try to use uniform field names and then identify the field names as a way of mapping results. But these field names may be inconsistent—systolic blood pressure may be called "SYS," "SBP," "Systolic," "Sys BP"—or could be in different languages, or could be spelled wrong. In contrast, the present invention does not require mapping of data using the labels (e.g., field or record names) associated with the data sets themselves. Another benefit of the present invention is that it does not require the data to be arranged in any specific order within data sets. In different clinical trials, values in a specific panel may appear in a different order, but the invention can detect the correlation among the values as well as the statistical relationship among the records for that panel. For example, vitals data sets may not always begin with systolic and diastolic blood pressure, but may begin with heart rate. And although it is likely that systolic blood pressure would precede diastolic blood pressure, that it not necessarily how all the data sets are structured, and the system will be able to discern when that is the case.

In sum, the present invention takes data sets from multiple studies and clinical settings and using a set of rules, automatically performs calculations to place the data within a single, categorized, unified database that can later be used in other environments for analysis, prediction, regulatory filings, etc. And as more data sets are used, the categories and the rules can be refined.

Database generator 100 as well as unified database 200 itself may be implemented on a network, for example, over the Internet as a cloud-based service or hosted service, which may be accessed through a standard web service API (application programming interface).

Aspects of the present invention may be embodied in the form of a system, a computer program product, or a method. Similarly, aspects of the present invention may be embodied as hardware, software or a combination of both, and may run on or with a processor. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A computer-implemented method for generating a unified clinical database, comprising:
   receiving a structured set of clinical data, the set comprising one or more records, each record having one or more fields;
   aggregating values taken from a first field of the records;
   calculating a statistical distribution of the aggregated first field values;

comparing the statistical distribution of the aggregated first field values with statistical distributions of stored data measures;

calculating a confidence level regarding a label for the first field;

if the confidence level meets or exceeds a pre-determined threshold,
providing the label to the first field; and
storing the first field values in a first unified field in the unified database; and if the confidence level does not exceed the pre-determined threshold, receiving more information and recalculating the confidence level, wherein providing the label to the first field comprises determining a data measure having a statistical distribution closest to the statistical distribution of the aggregated first field values.

2. The method of claim 1, further comprising calculating the statistical distributions of the stored data measures.

3. The method of claim 1, further comprising applying to the aggregated first field values a set of rules including eligibility criteria comprising inclusion criteria, exclusion criteria, or both.

4. A computer-implemented method for generating a unified clinical database, comprising:

receiving a structured set of clinical data, the set comprising one or more records, each record having two or more fields;

aggregating values taken from a first field of the records;
aggregating values taken from a second field of the records;
calculating statistical distributions of the aggregated first and second field values;

comparing the statistical distributions of the aggregated first and second field values with statistical distributions of stored data measures;

automatically applying, by a processor, a set of rules to the aggregated first and second field values to determine correlations between the aggregated first and second field values; and determining labels for the aggregated first and second field values based on the rules and the correlations, by:

determining a confidence level regarding a label for the first field;

if the confidence level meets or exceeds a pre-determined threshold, providing the label to the first field; and
storing the first field values in a first unified field in the unified database;
and if the confidence level does not exceed the pre-determined threshold, receiving more information and recalculating the confidence level.

5. The method of claim 4, wherein the more information comprises information regarding the correlations between the aggregated first and second field values.

6. The method of claim 4, wherein determining labels for the aggregated first and second field values comprises:

calculating a second confidence level regarding a label for the second field;

if the second confidence level meets or exceeds a pre-determined threshold, providing the label to the second field; and
storing the second field values in a second unified field in the unified database;
and if the second confidence level does not exceed the pre-determined threshold, receiving more information and recalculating the second confidence level.

7. The method of claim 6, wherein the more information comprises information regarding the correlations between the aggregated first and second field values.

8. The method of claim 4, wherein determining labels for the aggregated first and second field values comprises determining data measures having statistical distributions closest to the statistical distributions of the aggregated first and second field values.

9. The method of claim 4, wherein applying the set of rules to the aggregated first and second field values comprises determining a structure of the records.

10. The method of claim 9, wherein the structure of the records of a CHEM-7 test comprises seven fields.

11. The method of claim 4, wherein determining a confidence level regarding a label for the first field comprises calculating the confidence level.

12. A computer-implemented method for generating a unified clinical database, comprising:

receiving a structured set of clinical data, the set comprising one or more records, each record having one or more fields;

aggregating values taken from a first field of the records;
automatically applying, by a processor, a set of rules to the aggregated first field values, wherein applying the set of rules includes comparing the aggregated first field values to:

stored statistics of known clinical measures, if the aggregated first field values comprise numerical values;

known text entries from a clinical dictionary, if the aggregated first field values comprise alphabetical and alphanumeric values; and stored calendar information, if the aggregated first field values comprise date values;

calculating a confidence level regarding a label for the first field;

if the confidence level meets or exceeds a pre-determined threshold, providing the label to the first field; and
storing the first field values in a first unified field in the unified database; and if the confidence level does not exceed the pre-determined threshold, receiving more information and recalculating the confidence level.

13. The method of claim 12, wherein the rules include eligibility criteria comprising inclusion criteria, exclusion criteria, or both.

14. The method of claim 12, wherein the rules are refined based on the received data.

15. The method of claim 12, wherein the stored statistics comprise statistical distributions of known clinical measures.

16. The method of claim 12, wherein if the aggregated first field values comprise date values, and the date values are after the beginning of a clinical trial, then the first field label refers to testing during the clinical trial.

17. The method of claim 12, wherein if the aggregated first field values comprise date values, and the date values are before the beginning of a clinical trial, then the first field label refers to historic data.

18. The method of claim 12, further comprising:
aggregating values taken from a second field of the records;
automatically applying the set of rules to the aggregated second field values to determine correlations between the aggregated first and second field values; and
determining a label for the second field values.

19. The method of claim 18, wherein said correlations increase the confidence level regarding the label for the first field values.

\* \* \* \* \*